United States Patent [19]

Hetland

[11] Patent Number: 4,778,463
[45] Date of Patent: Oct. 18, 1988

[54] ARTIFICIAL INTRAOCULAR LENS

[76] Inventor: Jens Hetland, Trosteveien 16, N-1340 Bekkestua, Norway

[21] Appl. No.: 68,846

[22] Filed: Jul. 1, 1987

[30] Foreign Application Priority Data

Jul. 10, 1986 [NO] Norway .................................. 862796

[51] Int. Cl.$^4$ ............................................... A61F 2/16
[52] U.S. Cl. .................................................. 623/6
[58] Field of Search ............................................ 623/6

[56] References Cited

U.S. PATENT DOCUMENTS 4,666,444  5/1987  Pannu ...................................... 623/6

FOREIGN PATENT DOCUMENTS 0175972  4/1986  European Pat. Off. ................ 623/6

Primary Examiner—Ronald L. Frinks
Attorney, Agent, or Firm—Darby & Darby

[57] ABSTRACT

An artificial intraocular lens comprising an optical medial body means (optical part) and a supporting peripheral body means (haptic part) in the shape of at least two loops, being integral with and projecting from said optical part, the optical part being provided with two or more small peripherally provided first apertures and each of said loops being provided with a second aperture at a distance from or at the outer end of said loop. One of said first apertures is provided in the root of the loop. The lateral portion of the root of said loop facing away from said loop is shaped with a convacity that is essentially complementary to a portion of another opposite loop in which said second aperture is provided. The concavity and complementary portion of the loop are shaped and dimensioned for non-capture engagement when touch directly together in response to loop flexing. Said first aperture in the root of the loop and said second aperture in the closest loop form corresponding apertures which may be pulled together by the aid of a suture. Alternatively, said second aperture of said loops may be used to pull the loops toward the optical part. Utilization especially for implantation inside the lens bag of an eye.

4 Claims, 2 Drawing Sheets

ARTIFICIAL INTRAOCULAR LENS

The present invention relates to an artificial intraocular lens comprising an optical medial body means (optical part), and a supporting peripheral body means (haptic part) in the shape of at least two loop means which are integral with the optical part and project from the latter. The optical part is provided with two or more peripheral first apertures, and each of said loops at the root thereof is provided with one of said first apertures, and said loops are each provided with a second aperture each at a distance from or at the outer end of the loop.

The invention especially concerns artificial lenses for the human eye which are produced from acrylic (PMMA). It is, however, not intended to limit the invention to production of lenses from this material.

An artificial eye lens (IOL) is used to replace the human eye lens when the latter is removed due to vision impaired by darkening. Such darkening is called cataract. The cause of cataract may be "age", disease, or injury.

The medical term for an artificial lens of the mentioned kind is an artificial intraocular lens. The popular international medical term is IOL. Consequently, the term IOL will be used below.

IOL means produced for PMMA are used in eye surgery since 1949. In recent years a rather explosive development in all industrial countries has been experienced.

IOL means are in principle ranged in two main groups, i.e.:
(1) camera anterior-IOL, and
(2) camera posterior-IOL.
Camera posterior-IOL means comprise two kinds:
(2a) with loops to be fastened in the sulcus proper, and
(2b) with loops to be fastened inside the lens capsule.

The natural anatomic position of an IOL means is inside the lens bag after removal of the lens nuclens and cortex. The lens bag or lens capsule is, in fact, transparent and does not represent an optical obstruction. By the very fact that the lens bag is not removed the eye retains its natural partition between the anterior and posterior regions of the eye. This will cause less complications than is the case when the cataract is completely removed with the lens bag. The natural barrier between the anterior and posterior regions of the eye would then be broken.

The invention especially concerns IOL means intended to be placed in the lens bag proper, i.e. the above mentioned group 2b. When IOL is mentioned below it should, thus, be understood to be related to the above group 2b.

Today, there is a plurality of different models of IOL means. It is common to them all that they comprise a optical medial body means (optical part), and a supporting peripheral body means (haptic part) in the shape of loops.

In connection with implanting an IOL means the great problem is to have the haptic part inserted into the lens bag. Post examinations in several examination materials show that one of the loops often stays outside the lens bag proper. This is undesirable for various reasons, probably especially because the optical body will then have an asymmetric position in relation to the optical axis of the eye. Also, a loop or loops remaining outside the lens bag will contact iris tissue and, at worst, cause injury or irritation.

A series of special instruments and techniques are developed to aid the surgeon in placing IOL means in the lens bag. In most IOL means small apertures are provided both in the optical part and in the haptic body. By the aid of instruments the surgeon can engage these apertures to adjust the lens position inside the lens bag.

Also, IOL means were developed the loops of which can be locked mechanically to the optical part during implantation, and can then be released inside the lens bag. Coburn ®, model 75 is an example of such means. Mechanical locking of the loops before the lens is inserted does not involve special problems, but there will be difficulties when the locking mechanism is to be released inside the lens bag. Research is continued at Coburn in this field.

In all kinds of eye surgery needle and thread constitute an essential and obvious aid. The wound in the eye is, thus, sewn together by the aid of a thread that is barely visible to the naked eye (nylon 10 - 0 ). In fact, nothing could be more natural than utilizing needle and thread, below called suture, to join the loops (the haptic part) before implantation, and then to cut the suture when the IOL is in place in the lens bag.

In order to be able to do so, it is necessary that the suture aperture in the loop or haptic part is located at a rather fixed place in relation to the suture aperture in the optical body means.

For the loops to be squeezed together as much as possible, the suture aperture in the haptic part must be placed in a position that is determined by the suture aperture in the optical part when the haptic part is close to the optical part. The suture apertures then must correspond, and the distance between them must be minimal. Said two suture apertures may, thus, be termed corresponding apertures. In case of an IOL having two symmetrical loops there will, thus, be two pairs of corresponding apertures, i.e. four suture apertures totally. With more than two loops there would have to be more than two pairs of suture apertures.

In order to achieve a lever that is as long as possible, to thereby the moment of force, it is necessary to place the aperture in the loop as close to the periphery as possible.

According to the invention the above mentioned intraocular lens is characterized in that the portion of the root of each loop facing away from the loop is provided with a concavity being substantially complementary to a portion of another loop located opposite and in which said second hole is located, each loop having such extent that its said portion will touch directly against said concavity upon flexing of the loop toward the optical part of the lens. The concavity and complementary portion of the loop are shaped and dimensioned for non-capture engagement when touched directly together in response to loop flexing.

In order to achieve a lever of maximum length when the said parts are pulled together so as to reduce the moment of force the aperture in the loop must be placed as peripheral as possible. Its position will, thus, be determined by the localization of said lateral portion. When said second loop is close to the optical part of the configuration of the loop with said one suture aperture will be adapted to the loop root toward which the loop is flexed. When the loop is, thus, flexed towards the optical part said portion of the loop will get into contact with said concavity resulting in the distance between said corresponding apertures being in smallest.

Further characterizing features of the invention will appear from the following claims as well as from the disclosure below with reference to a preferred, but not limitative, embodiment of the invention.

Figure 1:
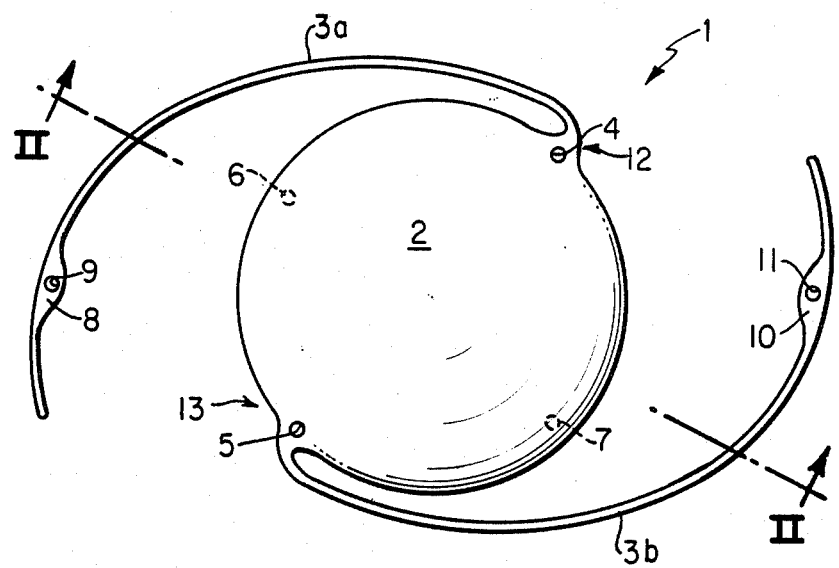
FIG. 1 illustrates the intraocular lens according to the invention.

In FIG. 1 the intraocular lens 1 according to the invention is illustrated. For simplicity it is called an IOL below. IOL 1 comprises an optical part 2 and a haptic part in the shape of two loops 3a and 3b. The optical part 2 is provided with small peripherally arranged first apertures 4, 5, provided in the root of loops 3a, and 3b, respectively, as will appear from FIG. 1. If desired, there may be provided further small first apertures 6, 7 which may possibly be of further aid in case of adjustment of the position of the IOL 1 in the lens bag.

Figure 3:
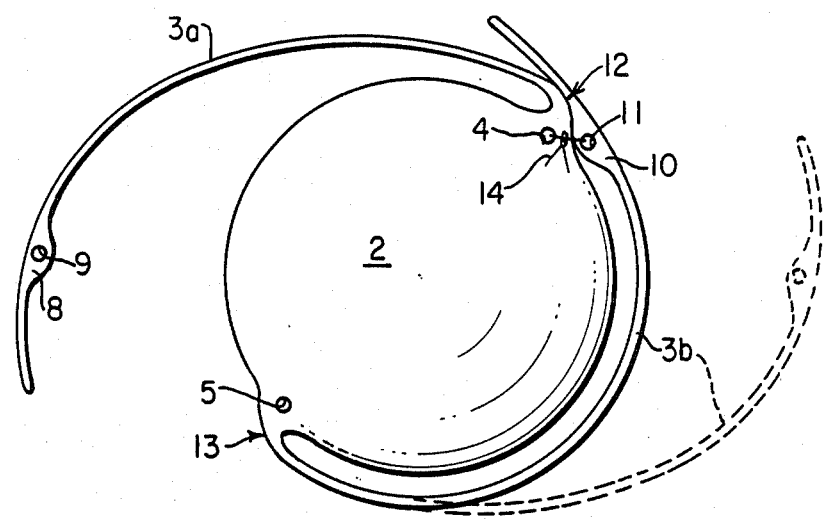
FIG. 3 illustrates the intraocular lens according to the invention with one of the loops pulled inwards towards the optical part.

At its free end loop 3a is provided with a portion 8 in which there is an aperture 9. In a similar manner a portion 10 with an aperture 11 is provided at the free end of loop 3b. Said apertures 9 and 11 constitute said second apertures of the intraocular lens. Apertures 4, 11 and 5, 9 are termed corresponding apertures, respectively. At the root of loop 3a a portion 12 of the loop is concavely shaped and essentially complementary to portion 10 of loop 3b. In a similar manner there is a lateral portion 13 at the root of loop 3b facing loop 3a and being concave and essentially complementary to portion 8 of loop 3a. When one or both loops are flexed inwardly said corresponding apertures will be as close to one another as possible, and at the same time the loop or loops will extend as closely as possible to the optical part 2, as will appear from FIGS. 3 and 4. In the embodiment shown in FIG. 3 the corresponding apertures 4, 11 between the optical part 2 and loop 3b are joined by the aid of a suture 14. In many cases it will not be necessary to connect apertures 5, 9 by a suture, since loop 3b is in this case the first to be inserted into the lens bag. In FIG. 3 loop 3b is indicated by a dashed line to illustrate its original position before the surgeon pulls loop 3b into contact with concavity 12 and the suture connection between corresponding apertures 4, 11.

Figure 4:
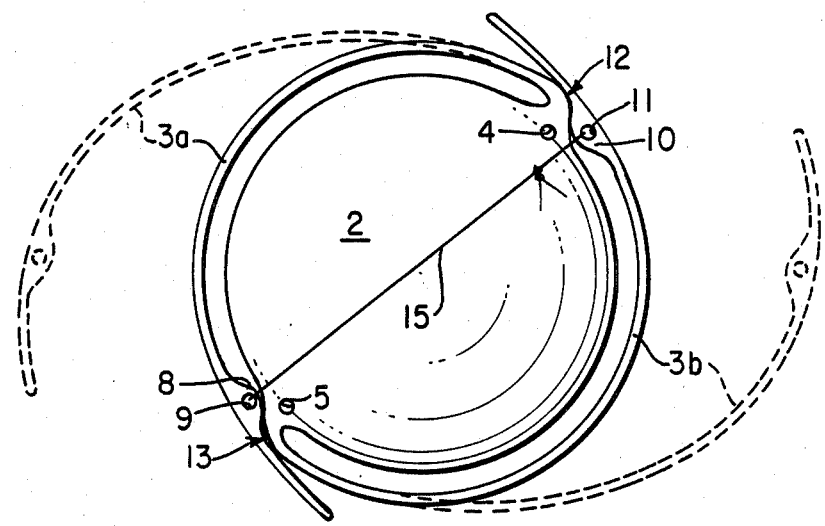
FIG. 4 illustrates the intraocular lens according to the invention with both loops pulled inwards toward the optical part.

In some case it may be advantageous to the place of operation or the surgery technique that both loops 3a and 3b are flexed in towards the optical part 2. In this case, as illustrated in FIG. 4, it will be sufficient to connect apertures 9 and 11 in loops 3a and 3b respectively, by suture 15. As shown in FIG. 4 portion 10 will contact the concave portion 12 on optical part 2 and, correspondingly, portion 8 on loop 3a will contact the concave portion 13 on the optical part 2. Obviously, it is possible, as vaguely indicated in connection with FIG. 3, that the loops are flexed inwardly toward the optical part, and are secured by the aid of a suture between said corresponding apertures 4, 11 and 5, 9, respectively. It will, however, be understood that the solution shown in FIG. 4 will be sufficient in this case and, additionally, have the great advantage that only one suture must be cut to release loops 3a and 3b from each other for engagement with the lens bag.

In the shown solution according to the invention it will, thus, be understood that it is important to provide the corresponding apertures 4, 11 and 5, 9, respectively, in order to be able to pull loops 3a, 3b as close as possible to the optical part 2 while said IOL is placed in the lens bag. Due to the fact that the root of the loop is provided with said concavity 12 and 13, respectively it is possible to pull the loop further inwards toward the optical part 2 to bring said corresponding apertures 4, 11 and 5, 9, respectively, closer together. Consequently, the maximum cross sectional dimension of IOL is also reduced, which is of great importance to an unproblematic insertion of IOL into the lens bag of the eye.

With the present invention the problems connected with flexing the loops inwards are avoided, simply due to surgeon, before the intraocular lens is inserted, providing the suture 14 or suture 15 are illustrated in FIG. 3 or FIG. 4, respectively while the lens lies on a sterile support. Then, the lens can be inserted into the lens bag whereafter the suture is cut and removed.

It should be understood that the configuration of the root 12 and 13, respectively, and the mass or portion 8 and 10, respectively, about apertures 9 and 11, respectively on loop 3a and loop 3b, respectively, can show variations of the design without changing the principle of corresponding suture apertures 4, 11 and 5, 9. The position of the corresponding suture apertures of an IOL are, thus, determined by the root of the loop. When the loop extends adjacent to the optical part the loop configuration with one suture aperture must be adapted to the root of another loop. The distance between the corresponding suture apertures will then be smallest.

It will be understood that the present invention can be used in connection with intraocular lenses provided with more than two loops, e.g. three or four loops. In case of 3 loops it may be suitable to use separate suture joining for two of the loops whereas the third loop is not tied inwards towards the optical part. In a solution with four loops, two pairs of diametrically placed loops may, e.g. be connected in such a manner as shown in FIG. 4, and it will be obvious that two sutures will be needed which form a mutual angle of 90°.

The above mentioned embodiments and alternatives are only meant as illustrative examples, and it will be understood that the surgeon is free to choose the most suitable suture connection for the loops, in consideration of the technique of surgery and other surgical conditions.

Figure 2:
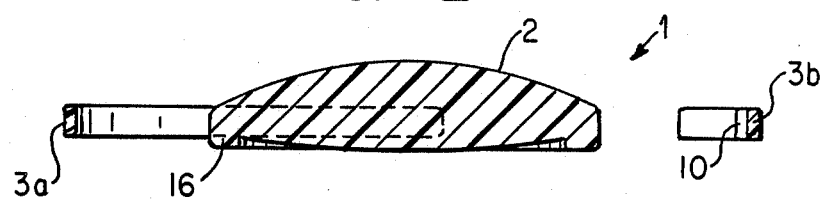
FIG. 2 shows the section II—II in FIG. 1.

It appears from FIG. 2 that the lens can be double convex in a manner known per se, and that it may be provided with a peripherally extending bead 16, a so-called laser-ring. The object of the laser-ring is to prevent the lens 2 from being damaged in case of a possible later treatment of the lens bag with laser in order to remove any residual tissue or further darkening due to insufficient cleaning or stripping of the lens bag before implantation of the IOL. Utilization of laser-rings is known per se.

Having described my invention, I claim:

1. In an artificial intraocular lens having an optical medial body means (optical part), and a supporting peripheral body means (haptic part) in the shape of at least two loops integral with and projecting from said optical part at roots thereof, said optical part being provided with two or more small peripherally-provided first apertures, and each of said loops at the root thereof being provided with one of said first apertures, and said loops each being provided with a second aperture at a distance from said first aperture, the improvement comprising that said loops have a portion facing toward the optical part and a portion facing away from the optical part, and that a lateral portion of the root of each loop facing away from the optical part is provided with a concavity being substantially complementary to a portion of another loop facing toward said optical part, said complementary portion being located opposite said concavity and in which said second hole is located, each loop having an extent such that its said complementary portion will touch directly against said concavity upon flexing of the loop toward the optical part of the lens, said concavity and said complementary portion being shaped and dimensioned for non-capture engagement when touched directly together in response to loop flexing.

2. A lens as defined in claim 1, wherein said loops are located and flexible in one and the same plane, each said loop having such an extent that when flexed toward the optical part of the lens its said portion will contact said concavity directly.

3. A lens as defined in claim 1 wherein the loops are dimensioned and designed for implantation of the lens inside the lens bag of the eye.

4. A lens as defined in claim 1, including means for using the first and second apertures for tying at least one haptic part to the optical part of the lens.

* * * * *